(12) United States Patent
Arai et al.

(10) Patent No.: US 11,134,923 B2
(45) Date of Patent: Oct. 5, 2021

(54) ULTRASONIC DIAGNOSTIC APPARATUS

(71) Applicant: SEIKO EPSON CORPORATION, Tokyo (JP)

(72) Inventors: Yoshio Arai, Shiojiri (JP); Masaki Hayashi, Matsumoto (JP)

(73) Assignee: Seiko Epson Corporation

( * ) Notice: Subject to any disclaimer, the term of this patent is extended or adjusted under 35 U.S.C. 154(b) by 356 days.

(21) Appl. No.: 16/089,314

(22) PCT Filed: Mar. 30, 2017

(86) PCT No.: PCT/JP2017/013239
§ 371 (c)(1),
(2) Date: Sep. 27, 2018

(87) PCT Pub. No.: WO2017/170865
PCT Pub. Date: Oct. 5, 2017

(65) Prior Publication Data
US 2019/0343491 A1   Nov. 14, 2019

(30) Foreign Application Priority Data

Apr. 1, 2016   (JP) .............................. JP2016-074030

(51) Int. Cl.
*A61B 8/08*   (2006.01)

(52) U.S. Cl.
CPC .................. *A61B 8/5269* (2013.01)

(58) Field of Classification Search
CPC . A61B 8/5269; A61B 8/5207; G01S 7/52026; G01S 7/52079; G01S 15/8915; G01S 7/52077
See application file for complete search history.

(56) References Cited

U.S. PATENT DOCUMENTS

| | | | |
|---|---|---|---|
| 2012/0065509 A1 | 3/2012 | Ziv-Ari et al. | |
| 2012/0113759 A1* | 5/2012 | Oshiki | A61B 8/00 367/178 |
| 2012/0281502 A1* | 11/2012 | Tsushima | G01S 7/52047 367/87 |
| 2015/0164483 A1* | 6/2015 | Miyajima | A61B 8/546 600/443 |

(Continued)

FOREIGN PATENT DOCUMENTS

| | | |
|---|---|---|
| JP | H02-036850 A | 2/1990 |
| JP | H02-286142 A | 11/1990 |

(Continued)

*Primary Examiner* — Christopher Koharski
*Assistant Examiner* — Kaitlyn E Selmer
(74) *Attorney, Agent, or Firm* — Harness, Dickey & Pierce, P.L.C.

(57) ABSTRACT

An ultrasonic diagnostic apparatus includes: a plurality of receiving elements that receive an ultrasonic wave, convert the ultrasonic wave into an electric signal, and output a receiving signal; a first detecting amplifier that detects noise and outputs a noise signal; a second detecting amplifier that amplifies the noise signal and outputs an amplified noise signal; a subtraction amplifier that receives the receiving signal and the amplified noise signal and subtracts the amplified noise signal from the receiving signal; and a plurality of circuit substrates that each include the second detecting amplifier and subtraction amplifier.

6 Claims, 7 Drawing Sheets

(56) References Cited

U.S. PATENT DOCUMENTS

2017/0150946 A1* 6/2017 Yoshizawa ........... A61B 8/4494

FOREIGN PATENT DOCUMENTS

| JP | H06-063044 A |   | 3/1994 |
|----|--------------|---|--------|
| JP | H06-296610 A |   | 10/1994 |
| JP | H07-170454 A |   | 7/1995 |
| JP | 2004-337341 A |   | 12/2004 |
| JP | 2006-158732 A |   | 6/2006 |
| JP | 2007-159781 A |   | 6/2007 |
| JP | 2007-208549 A |   | 8/2007 |
| JP | 2008-245705 A |   | 10/2008 |
| JP | 2009-261441 A |   | 11/2009 |
| JP | 2010-240131 A | * | 10/2010 |
| JP | 2012-055692 A |   | 3/2012 |

* cited by examiner

ULTRASONIC DIAGNOSTIC APPARATUS

CROSS-REFERENCE TO RELATED APPLICATIONS

This application is a U.S. National Stage Application of International Application No. PCT/JP2017/013239, filed Mar. 30, 2017, and published in Japanese as WO 2017/170865 A1 on Oct. 5, 2017, which claims priority to Japanese Patent Application No. 2016-074030, filed on Apr. 1, 2016. The entire disclosures of the above applications are incorporated herein by reference.

BACKGROUND

Technical Field

The present invention relates to an ultrasonic diagnostic apparatus.

Related Art

There has been widely used an ultrasonic diagnostic apparatus that emits an ultrasonic wave toward an internal part of a subject and generates an ultrasonic image by using an ultrasonic wave reflected from the internal part of the subject. The reflected ultrasonic wave is converted into an electric signal by a transducer. The electric signal is a weak signal and is amplified by an amplifier circuit. At this time, various types of noise such as electromagnetic noise or power-source noise are included in the amplified signal.

When a noise component is large, it is difficult to have a clear view of the ultrasonic image. In this respect, JP-A-2010-240131 discloses a method for reducing noise. According to JP-A-2010-240131, an ultrasonic diagnostic apparatus includes a preprocessing substrate on which a subtraction amplifier is mounted and the subtraction amplifier subtracts a noise signal from an ultrasonic signal. In this manner, the preprocessing substrate converts a receiving signal of an ultrasonic wave into a signal having a small noise component. Thus, the ultrasonic diagnostic apparatus realizes a display of the ultrasonic image having low noise.

An ultrasonic element array, in which receiving elements are disposed in a matrix shape, is installed in an ultrasonic probe. In order to increase the resolution of the ultrasonic image, the number of receiving elements is increased. When a circuit configuration of JP-A-2010-240131 is applied, the number of subtraction amplifiers is increased, and thus it is necessary to increase an area of a circuit substrate. Thus, a control device becomes a large device. As a countermeasure, the circuit substrate is divided into a plurality of circuit substrates. At this time, noise having a different phase for each circuit substrate due to the impedance of wiring, through which the circuit substrates are connected, is superimposed on a receiving signal in some cases. In this respect, there has been a demand for an ultrasonic diagnostic apparatus that is capable of effectively reducing noise that is included in the receiving signal even when the phase of the noise that is included in the receiving signal is different for each circuit substrate.

SUMMARY

The present invention is made to solve such a problem described above and can be realized in the following aspects or application examples.

Application Example 1

An ultrasonic diagnostic apparatus according to this application example includes: a plurality of receiving elements that receive an ultrasonic wave, convert the ultrasonic wave into an electric signal, and output a receiving signal; a noise detecting unit that detects noise and outputs a noise signal; a noise signal amplifying unit that amplifies the noise signal and outputs an amplified noise signal; a subtracting unit that receives the receiving signal and the amplified noise signal and subtracts the amplified noise signal from the receiving signal; and a plurality of circuit substrates, each of which has the noise signal amplifying unit and the subtracting unit.

According to this application example, the ultrasonic diagnostic apparatus includes the plurality of receiving elements, the plurality of noise detecting units, and the plurality of circuit substrates. The circuit substrate has the noise signal amplifying unit and the subtracting unit. The receiving element receives the ultrasonic wave, converts the ultrasonic wave into the electric signal, and outputs the receiving signal. The noise detecting unit detects noise and outputs the noise signal to the noise signal amplifying unit. The noise signal amplifying unit amplifies the input noise signal and outputs the amplified noise signal to the subtracting unit. The subtracting unit receives the receiving signal and the amplified noise signal and subtracts the amplified noise signal from the receiving signal. In this manner, even when the receiving signal includes unnecessary noise, it is possible to reduce the noise that is included in the receiving signal. The noise signal amplifying unit is installed for each circuit substrate. Hence, the noise signal that is subtracted from the receiving signal changes for each circuit substrate. As a result, even when a phase of the noise that is included in the receiving signal is different for each circuit substrate, it is possible to effectively subtract the noise that is included in the receiving signal.

Application Example 2

The ultrasonic diagnostic apparatus according to the application example described above, further includes: a storage unit that stores a predetermined coefficient, and the subtracting unit subtracts a calculation result obtained by multiplying the amplified noise signal by the coefficient from the receiving signal.

According to this application example, the storage unit that stores the predetermined coefficient is provided. Thus, the subtracting unit subtracts the calculation result obtained by multiplying the amplified noise signal by the coefficient from the receiving signal. Hence, it is possible to subtract the calculation result obtained by multiplying the amplified noise signal by each individual coefficient for each subtracting unit from the receiving signal. As a result, it is possible to easily adjust an amount that is subtracted from the receiving signal.

Application Example 3

In the ultrasonic diagnostic apparatus according to the application example described above, the receiving elements are arranged in one direction, and the coefficient corresponding to the receiving signal output from the receiving element that is positioned at the center is larger than the coefficient corresponding to the receiving signal output from the receiving element that is positioned at the end.

According to this application example, the receiving elements are arranged in one direction. Therefore, the receiving elements include a receiving element that is positioned in a portion at an end of an arrangement and a receiving element that is positioned in a portion at the center of the arrangement. A noise signal that is included in the receiving signal which is output by the receiving element positioned in the portion of the center of the arrangement is referred to as a noise signal of the central portion. A noise signal that is included in the receiving signal which is output by the receiving element positioned in the portion at the end of the arrangement is referred to as a noise signal of the end portion. At this time, the noise signal of the central portion is larger than the noise signal of the end portion.

A receiving signal which is output by the receiving element positioned in the portion of the center of the arrangement is referred to as a receiving signal of the central portion. A receiving signal which is output by the receiving element positioned in the portion of the end of the arrangement is referred to as a receiving signal of the end portion. Thus, the coefficient corresponding to the receiving signal of the central portion is larger than the coefficient corresponding to the receiving signal of the end portion. Hence, the noise signal of the central portion is more reduced than the noise signal of the end portion. As a result, it is possible to obtain the receiving signal having an influence of noise which is reduced depending on the position of the arrangement of the receiving elements.

Application Example 4

The ultrasonic diagnostic apparatus according to the application example described above further includes: a coefficient calculating unit that calculates the coefficient from a distribution of noise signals for reference, which are output from receiving elements when an ultrasonic reflection signal is not detected.

According to this application example, the ultrasonic diagnostic apparatus further includes the coefficient calculating unit. Thus, the coefficient calculating unit calculates the coefficient from the distribution of noise signals for reference, which are output from the receiving elements when an ultrasonic reflection signal is not detected. Hence, it is possible to calculate the coefficient corresponding to the unique distribution of the noise signals for reference for each arrangement of the receiving elements. As a result, it is possible to subtract the noise signal from the receiving signal with higher accuracy.

Application Example 5

In the ultrasonic diagnostic apparatus according to the application example described above, the noise detecting unit includes a noise detecting element that outputs the noise signal, and the noise detecting element and the receiving element have the same structure.

According to this application example, the noise detecting unit includes the noise detecting element that outputs the noise signal. The noise detecting element and the receiving element have the same structure. Hence, the noise detecting element is capable of detecting a noise signal having the same intensity as the noise signal that is included in the receiving signal which is output by the receiving element.

Application Example 6

In the ultrasonic diagnostic apparatus according to the application example described above, the noise detecting element and the receiving element are installed in a substrate, and a thickness of the substrate at a position opposite to the receiving element is smaller than a thickness of the substrate at a position opposite to the noise detecting element.

According to this application example, the noise detecting element and the receiving element are installed on the substrate. Thus, the thickness of the substrate at the position opposite to the receiving element is small and the substrate vibrates due to the ultrasonic wave at the position. On the other hand, the thickness of the substrate at the position opposite to the noise detecting element is large and the substrate is unlikely to vibrate due to the ultrasonic wave at the position. Hence, the receiving element receives the ultrasonic wave, the noise detecting element is unlikely to be influenced by the ultrasonic wave, and thus it is possible to easily detect the noise.

Application Example 7

In the ultrasonic diagnostic apparatus according to the application example described above, the circuit substrate is provided with a switching circuit installed to supply a power source.

According to this application example, the circuit substrate is provided with the switching circuit installed to supply the power source. Since the noise signal amplifying unit and the subtracting unit are provided on the circuit substrate, the circuit installed on the circuit substrate can reduce the noise signal. Thus, since the switching circuit that supplies the power source is installed for each circuit substrate, it is possible to easily supply a predetermined voltage to each circuit substrate.

Application Example 8

An ultrasonic diagnostic apparatus according to this application example includes: a plurality of receiving elements that receive an ultrasonic wave, convert the ultrasonic wave into an electric signal, and outputs a receiving signal; a plurality of noise detecting elements that detect noise and output a noise signal; and subtracting units that receive the receiving signal and the noise signal and subtract the noise signal from the receiving signal. One receiving element, one noise detecting element, and one subtracting unit configure one set, and the receiving element and the noise detecting element in the same set are disposed to be adjacent to each other.

According to this application example, one receiving element, one noise detecting element, and one subtracting unit configure one set. The receiving element and the noise detecting element in the same set are disposed to be adjacent to each other. Equivalent electromagnetic noise is applied to both of the adjacent receiving element and noise detecting element. Thus, the subtracting unit can remove, from the receiving signal, a noise signal equivalent to the noise signal that is added to the receiving signal. Hence, it is possible to remove the noise signal from the receiving signal with high accuracy.

Application Example 9

The ultrasonic diagnostic apparatus according to the application example described above further includes a transmitting element that transmits an ultrasonic wave intermittently, and the transmitting element serves as a noise detecting element that outputs the noise signal when the transmitting element does not transmit an ultrasonic wave.

According to this application example, the ultrasonic diagnostic apparatus includes the transmitting element that transmits the ultrasonic wave intermittently. The transmitting element serves as the noise detecting element that outputs the noise signal when the transmitting element does not transmit the ultrasonic wave. Hence, the noise detecting element may be provided separately from the transmitting element, and thus it is possible to manufacture the ultrasonic diagnostic apparatus with high productivity.

DETAILED DESCRIPTION

Hereinafter, embodiments will be described with reference to the figures. Members shown in the figures have a size to the extent that the members are recognizable on the figures, and thus a different scale is applied for each of the members on the figures.

First Embodiment

Figure 1:
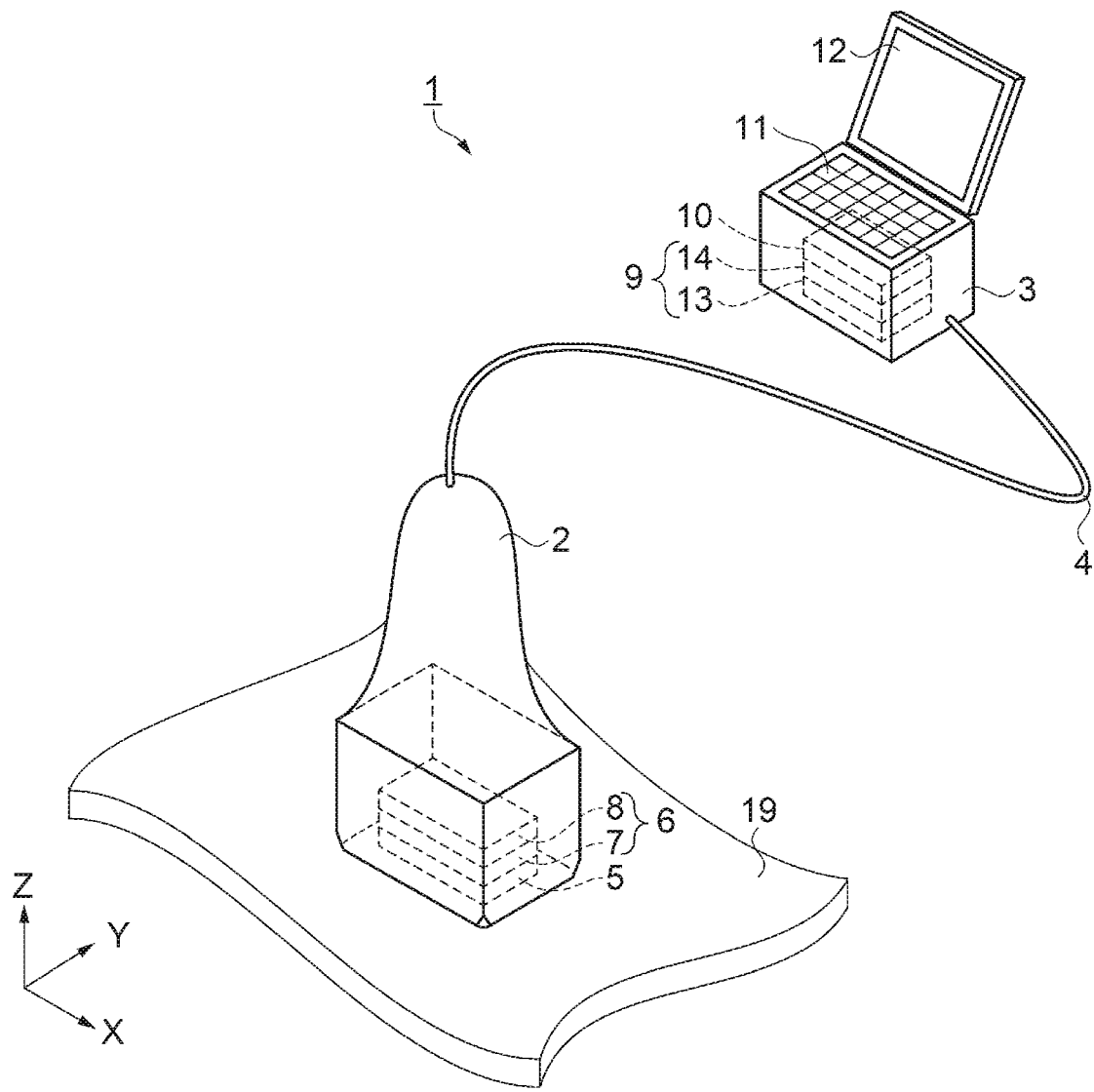
FIG. 1 is a schematic perspective view showing a configuration of an ultrasonic diagnostic apparatus according to a first embodiment.

In the embodiment, a characteristic example of a circuit in an ultrasonic diagnostic apparatus is described with reference to the figures. The ultrasonic diagnostic apparatus according to the first embodiment is described with reference to FIGS. 1 and 2. FIG. 1 is a schematic perspective view showing a configuration of the ultrasonic diagnostic apparatus. As shown in FIG. 1, an ultrasonic diagnostic apparatus 1 includes an ultrasonic probe 2 and a control device 3. The ultrasonic probe 2 and the control device 3 are connected to each other via a cable 4. An operator uses by making the ultrasonic probe 2 come into contact with a subject 19.

The ultrasonic probe 2 includes an ultrasonic element array 5 and a relay substrate 6. The ultrasonic element array 5 has ultrasonic elements which are disposed in a matrix shape. The ultrasonic element may be configured to have a transmitting element that transmits an ultrasonic wave and a receiving element that receives an ultrasonic wave or may be configured to have a transmitting/receiving element that transmits and receives the ultrasonic wave. In the embodiment, the ultrasonic element array 5 has a configuration in which the transmitting element and the receiving element are disposed.

The relay substrate 6 is configured to have a first relay substrate 7 and a second relay substrate 8. The relay substrate 6 is configured of a plurality of substrates, and the number of substrates is not particularly limited. In the embodiment, the relay substrate 6 is configured to have two substrates, for easy understanding of the description. The relay substrate 6 may be configured of three or more substrates. Some ultrasonic elements are connected to the first relay substrate 7, and the rest of the ultrasonic elements are connected to the second relay substrate 8. Thus, the relay substrate 6 is connected to the cable 4.

The control device 3 includes a preprocessing substrate 9 as a circuit substrate, a control substrate 10, an input unit 11, and a display unit 12. The preprocessing substrate 9 performs a noise removing process, an amplifying process, an analog/digital (A/D) converting process, and a parallel/serial converting process. The preprocessing substrate 9 is configured to have a first preprocessing substrate 13 as the circuit substrate and a second preprocessing substrate 14 as the circuit substrate. The preprocessing substrate 9 is configured of a plurality of substrates, and the number of substrates is not particularly limited. In the embodiment, the preprocessing substrate 9 is configured to have two substrates, for easy understanding of the description. The first relay substrate 7 outputs a signal to the first preprocessing substrate 13, and the second relay substrate 8 outputs a signal to the second preprocessing substrate 14.

The preprocessing substrate 9 may be configured of three or more substrates. It is preferable that the relay substrate 6 and the preprocessing substrate 9 have the same number of substrates. The circuit wiring can be simply configured. The relay substrate 6 and the preprocessing substrate 9 may have the different number of substrates.

The control substrate 10 is connected to the preprocessing substrate 9. The control substrate 10 performs signal processing, image processing, and display processing. The control substrate 10 is connected to the input unit 11 and the display unit 12 and outputs an image signal to the display unit 12. The input unit 11 is a keyboard, a mouse controller, or the like. An operator operates the input unit 11 and inputs content of instruction to the ultrasonic diagnostic apparatus 1. The display unit 12 displays an ultrasonic image or a measurement condition. It is possible to use, as the display unit 12, a liquid crystal display device, an organic electroluminescence display, a plasma display, or a surface field display.

Figure 2:
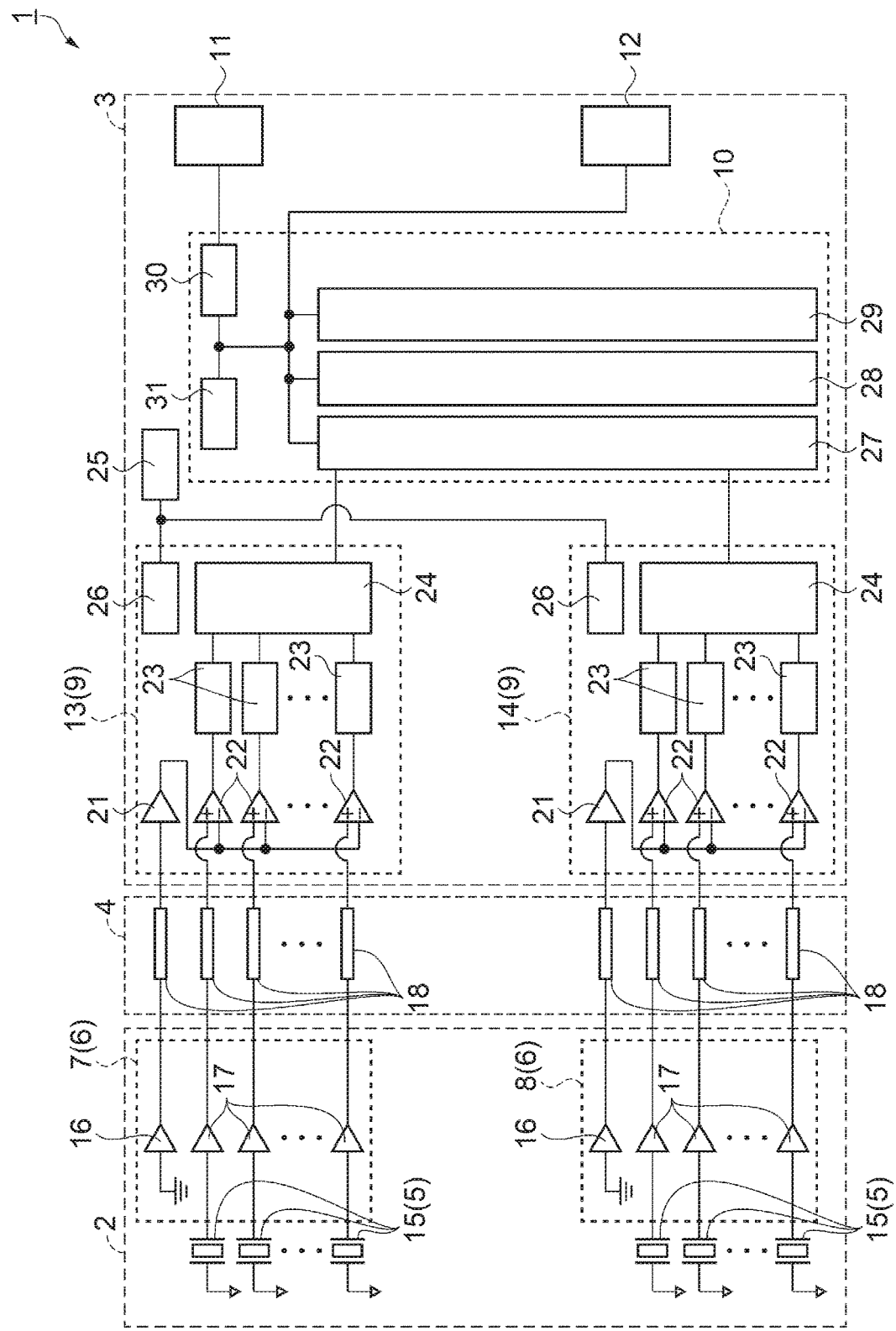
FIG. 2 is an electric circuit diagram of the ultrasonic diagnostic apparatus.

FIG. 2 is an electric circuit diagram of the ultrasonic diagnostic apparatus. As shown in FIG. 2, the ultrasonic element array 5, in which receiving elements 15 are arranged, the first relay substrate 7, and the second relay substrate 8 are installed in the ultrasonic probe 2. The receiving element 15 in the figures is an element that receives the ultrasonic wave. The receiving element 15 receives the ultrasonic wave, converts the ultrasonic wave into the electric signal, and outputs a receiving signal. The transmitting element that emits the ultrasonic wave is installed in the ultrasonic element array 5 but is omitted in the figures.

A plurality of amplifier circuits are installed in the first relay substrate 7. Each of the amplifier circuits has an input portion and an output portion. The input portion of one amplifier circuit is grounded to a housing. This amplifier circuit is a first detecting amplifier 16. The first detecting amplifier 16 amplifies noise that is input from the ground. The first detecting amplifier 16 corresponds to a noise detecting unit that detects the noise and outputs a noise signal.

An input portion of another amplifier circuit is connected to the receiving element 15. This amplifier circuit is a first ultrasonic wave amplifier 17. The first ultrasonic wave amplifier 17 amplifies a receiving signal that is output by the receiving element 15. Since the second relay substrate 8 has the same configuration as that of the first relay substrate 7, the description thereof is omitted. A plurality of shielded wires 18 are installed in the cable 4. Output portions of the first detecting amplifier 16 and the first ultrasonic wave amplifier 17 are connected to the shielded wire 18.

One second detecting amplifier 21 and a plurality of subtraction amplifiers 22 as subtracting units are installed on the first preprocessing substrate 13. An input portion of the second detecting amplifier 21 and the output portion of the first detecting amplifier 16 are connected to each other via the shielded wire 18. The second detecting amplifier 21 corresponds to a noise signal amplifying unit that amplifies the noise signal and outputs the amplified noise signal. An amplification factor of the second detecting amplifier 21 can be adjusted by a variable resistance or the like. The subtraction amplifier 22 is provided with a +input portion, a −input portion, and an output portion. The subtraction amplifier 22 subtracts a voltage input from the −input portion from a voltage input from the +input portion and outputs an obtained value to the output portion. The subtraction amplifier 22 can be designed by applying a difference amplifier thereto.

The number of subtraction amplifiers 22 installed on the first preprocessing substrate 13 is the same as the number of first ultrasonic wave amplifiers 17 installed on the first relay substrate 7. Thus, output portions of the first ultrasonic wave amplifiers 17 of the first relay substrate 7 are connected to the +input portions of the subtraction amplifiers 22 of the first preprocessing substrate 13 via the shielded wires 18. The −input portions of the subtraction amplifiers 22 are connected to the output portion of the second detecting amplifier 21 via wiring.

In this manner, the receiving signal is input to the +input portion of the subtraction amplifier 22, and the amplified noise signal is input to the −input portion thereof. Thus, the subtraction amplifier 22 corresponds to a subtracting unit that subtracts the amplified noise signal from the receiving signal. A signal obtained by calculation from the subtraction amplifier 22 is referred to as an ultrasonic signal. On the first preprocessing substrate 13, A/D converters 23 are installed, and the number of A/D converters is the same as the number of subtraction amplifiers 22. The A/D converter receives the ultrasonic signal that is output by the subtraction amplifier 22 and converts the ultrasonic signal into a digital signal.

A parallel/serial (P/S) converting circuit 24 is installed on the first preprocessing substrate 13. An output from each of the A/D converter 23 is parallel data, and the P/S converting circuit 24 converts the parallel data into serial data and transmits the serial data to the control substrate 10. Transmission of the serial data enables the number of data wirings to decrease. Thus, it is possible to decrease a space that is occupied by the wirings, and thus it is possible to decrease the control device 3 in size.

The control device 3 includes a power source unit 25, and the power source unit 25 supplies a DC voltage to the first preprocessing substrate 13 and the second preprocessing substrate 14. The power source unit 25 may receive an AC voltage and convert the AC voltage into the DC voltage or may include a rechargeable battery. A switching circuit 26 that supplies a power source is installed on the first preprocessing substrate 13 and the second preprocessing substrate 14. The switching circuit 26 receives the DC voltage and converts the DC voltage into a DC voltage having different voltage. Thus, the switching circuit 26 of the first preprocessing substrate 13 supplies the DC voltage to electric elements in the first preprocessing substrate 13 and the first relay substrate 7. Similarly, the switching circuit 26 of the second preprocessing substrate 14 supplies the DC voltage to electric elements in the second preprocessing substrate 14 and the second relay substrate 8.

A circuit configuration in the second preprocessing substrate 14 is the same as the circuit configuration in the first preprocessing substrate 13, and the second preprocessing substrate has the same function as that of the first preprocessing substrate. The preprocessing substrate 9 includes the second detecting amplifier 21 and the subtraction amplifier 22. Thus, the second preprocessing substrate 14 receives a noise signal and a receiving signal from the second relay substrate 8 and computes an ultrasonic signal obtained by subtracting the noise signal from the receiving signal. Further, the second preprocessing substrate 14 converts the ultrasonic signal into serial data of digital data and outputs the serial data to the control substrate 10. The amplification factor of the second detecting amplifier 21 is adjusted for each of the preprocessing substrates 9 and is individually set. Noise is detected for each of the preprocessing substrates 9. Thus, even when phase of noise that is input to the subtraction amplifier 22 is different for each of the preprocessing substrates 9, noise having a phase match is detected, and the subtraction amplifier 22 performs subtraction. Hence, the noise is appropriately reduced for each of the preprocessing substrates 9. The circuit configuration of the second preprocessing substrate 14 is the same as the circuit configuration of the first preprocessing substrate 13, and thus the detailed description of the second preprocessing substrate 14 is omitted.

A signal processing unit 27, an image processing unit 28, a display control unit 29, an integrated control unit 30, and a storage unit 31 are installed in the control substrate 10. The signal processing unit 27 receives the serial data from the first preprocessing substrate 13 and the second preprocessing substrate 14 and stores ultrasonic data of the receiving element 15 to the storage unit 31. The image processing unit 28 receives ultrasonic data and forms an ultrasonic image. The display control unit 29 converts the ultrasonic image into data that is driven by the display unit 12 and outputs the data to the display unit 12.

The integrated control unit 30 controls the signal processing unit 27, the image processing unit 28, and the display control unit 29. The input unit 11 is connected to the integrated control unit 30, and the integrated control unit 30 has a function of reflecting an instruction of an operator to a process of the image processing unit 28. The storage unit 31 stores data of various setting conditions, in addition to the ultrasonic data and the image data. The control substrate 10 may have the CPU, and the CPU may perform functions of the signal processing unit 27, the image processing unit 28, and the display control unit 29 in accordance with a program. At this time, the program is stored in the storage unit 31. The signal processing unit 27, the image processing unit 28, and the display control unit 29 may be configured of the electric circuit.

Next, a flow of a signal and data in the ultrasonic diagnostic apparatus 1 will be described. First, the transmitting element (not shown) emits the ultrasonic wave to the subject 19. The ultrasonic wave is reflected from an internal part of the subject 19, and a part of the ultrasonic wave reaches the receiving element 15. The receiving element 15 receives the ultrasonic wave, converts the ultrasonic wave into a receiving signal, which is the electric signal, and outputs the receiving signal to the first ultrasonic wave amplifier 17. The first ultrasonic wave amplifier 17 outputs the receiving signal to the subtraction amplifier 22 via the shielded wire 18.

The first detecting amplifier 16 outputs the noise signal to the second detecting amplifier 21 via the shielded wire 18. The second detecting amplifier 21 amplifies the noise signal and outputs the amplified noise signal to the subtraction amplifier 22. The subtraction amplifier 22 subtracts the amplified noise signal from the receiving signal and outputs the ultrasonic signal to the A/D converter 23. The A/D converter 23 converts the ultrasonic signal into the digital data and outputs the digital data to the P/S converting circuit 24. The P/S converting circuit 24 converts the digital data into serial digital data and outputs the serial digital data to the signal processing unit 27.

Receiving signals that are output from some receiving elements 15 installed in the ultrasonic element array 5 are output to the signal processing unit 27 through the first relay substrate 7, the cable 4, and the first preprocessing substrate 13. Receiving signals that are output from the rest of the receiving elements 15 installed in the ultrasonic element array 5 are output to the signal processing unit 27 through the second relay substrate 8, the cable 4, and the second preprocessing substrate 14.

The signal processing unit 27 receives serial data and outputs digital data of an ultrasonic signal. The image processing unit 28 outputs an ultrasonic image obtained by using the digital data of the ultrasonic signal. The display control unit 29 converts the ultrasonic image into data that is driven by the display unit 12 and outputs the data to the display unit 12. The display unit 12 displays the ultrasonic image.

As described above, according to the embodiment, the following effects are achieved.

(1) According to the embodiment, the ultrasonic diagnostic apparatus 1 includes the plurality of receiving elements 15, the plurality of first detecting amplifiers 16, and the plurality of preprocessing substrates 9. The preprocessing substrate 9 includes the second detecting amplifier 21 and the subtraction amplifier 22. The receiving element 15 receives the ultrasonic wave, converts the ultrasonic wave into the electric signal, and outputs the receiving signal to the subtraction amplifier 22. The first detecting amplifier 16 detects noise and outputs the noise signal to the second detecting amplifier 21. The second detecting amplifier 21 amplifies the input noise signal and outputs the amplified noise signal to the subtraction amplifier 22. The subtraction amplifier 22 receives the receiving signal and the amplified noise signal and subtracts the amplified noise signal from the receiving signal. In this manner, even when the receiving signal includes unnecessary noise, it is possible to reduce the noise that is included in the receiving signal. The noise signal amplifying unit is installed for each of the preprocessing substrates 9. Hence, the noise signal that is subtracted from the receiving signal changes for each of the preprocessing substrates 9. As a result, even when a phase of the noise that is included in the receiving signal is different for each of the preprocessing substrates 9, it is possible to effectively subtract the noise that is included in the receiving signal.

(2) According to the embodiment, the preprocessing substrate 9 is provided with the switching circuit 26 installed to supply the power source. Since the preprocessing substrate includes the second detecting amplifier 21 and the subtraction amplifier 22, and thus it is possible to reduce the noise signal. Since the switching circuit 26 that supplies the power source is installed in the preprocessing substrate 9, it is possible to easily increase the number of preprocessing substrates 9.

(3) According to the embodiment, the first relay substrate 7 and the first preprocessing substrate 13 are connected to each other via the cable 4, and the second relay substrate 8 and the second preprocessing substrate 14 are connected to each other via the cable 4. When noise is generated by the switching circuit 26 of the first preprocessing substrate 13, the noise is blocked in the first relay substrate 7 and the first preprocessing substrate 13. Therefore, it is possible to reduce the influence of the noise on the second detecting amplifier 21 and the subtraction amplifier 22 in the first preprocessing substrate 13.

Similarly, when noise is generated by the switching circuit 26 of the second preprocessing substrate 14, the noise is blocked in the second relay substrate 8 and the second preprocessing substrate 14. Therefore, it is possible to reduce the influence of the noise on the second detecting amplifier 21 and the subtraction amplifier 22 in the second preprocessing substrate 14. The noise generated by the switching circuit 26 has a different phase or voltage level for each substrate. Even in this case, since the noise is subtracted for each substrate, it is possible to reduce the noise with high accuracy.

(4) According to the embodiment, the relay substrate 6 is divided into the first relay substrate 7 and the second relay substrate 8. Hence, the first relay substrate 7 and the second relay substrate 8 are disposed to be opposite to each other, and thereby the ultrasonic probe 2 can be reduced in size so as to be easily held. Similarly, the preprocessing substrate 9 is divided into the first preprocessing substrate 13 and the second preprocessing substrate 14. Hence, the first preprocessing substrate 13 and the second preprocessing substrate 14 are disposed to be opposite to each other, and thereby the control device 3 can be reduced in size.

(5) According to the embodiment, the first detecting amplifier 16 is installed in the ultrasonic probe 2. Hence, even when the ultrasonic element array 5 receives electromagnetic noise, the first detecting amplifier 16 can detect the electromagnetic noise. As a result, it is possible to remove the electromagnetic noise from the ultrasonic signal.

(6) According to the embodiment, the input portion of the first detecting amplifier 16 is grounded. Hence, it is possible to detect circuit noise generated in the ultrasonic diagnostic apparatus 1. Thus, it is possible to reduce image noise.

Second Embodiment

Figure 3:
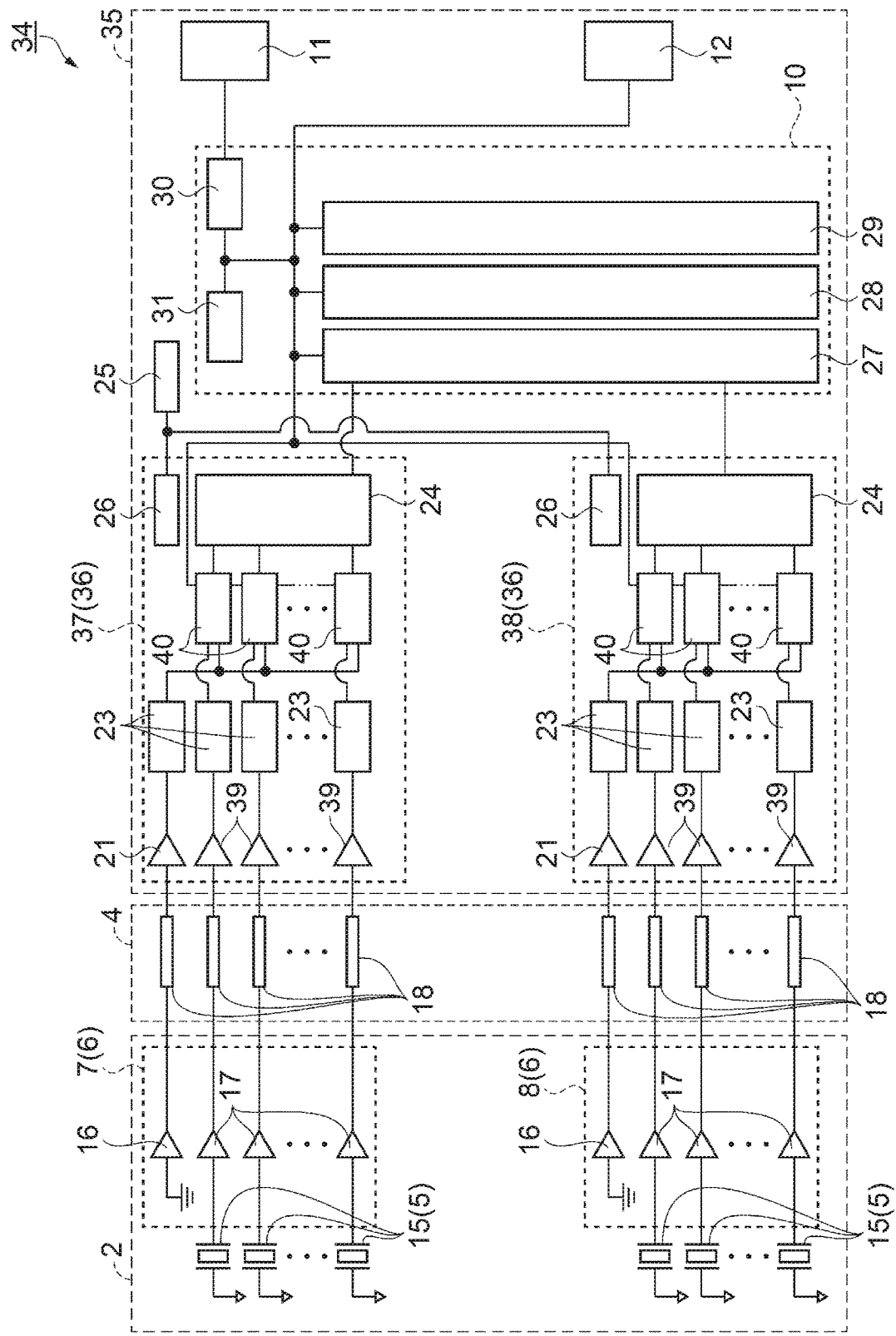
FIG. 3 is an electric circuit diagram of an ultrasonic diagnostic apparatus according to a second embodiment.
Figure 4:
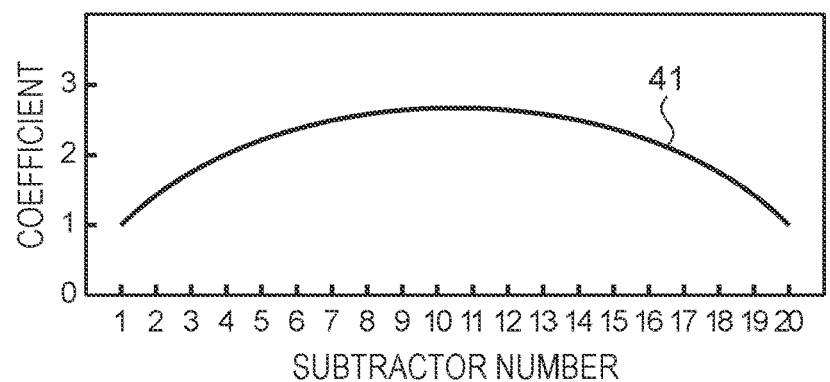
FIG. 4 is a graph for illustrating an operation of an electric circuit.
Figure 5:
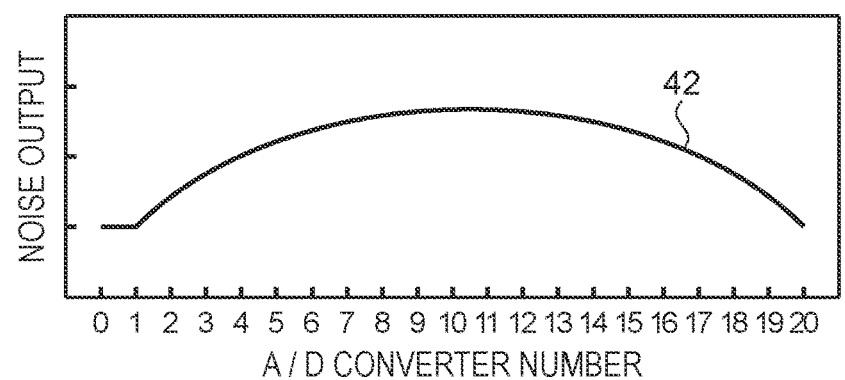
FIG. 5 is a graph for illustrating an operation of the electric circuit.
Figure 6:
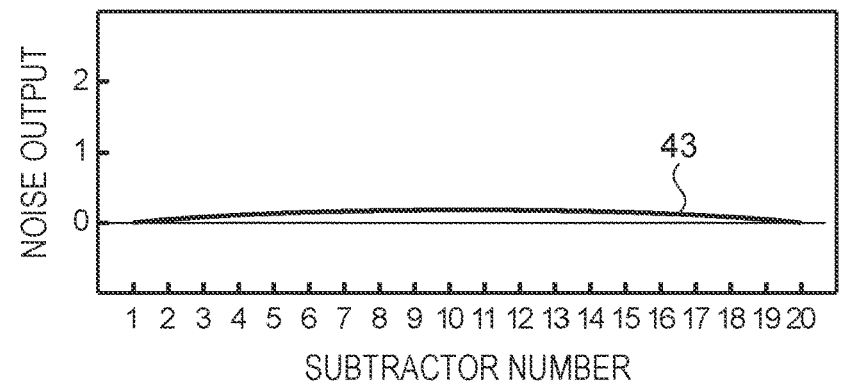
FIG. 6 is a graph for illustrating an operation of the electric circuit.

Next, an embodiment of the ultrasonic imaging apparatus will be described with reference to FIGS. 3 to 6. FIG. 3 is an electric circuit diagram of the ultrasonic diagnostic apparatus. FIGS. 4 to 6 are graphs for illustrating operations of the electric circuit. The embodiment differs from the first embodiment in that the receiving signal and the noise signal are converted into a digital signal, and then the noise signal is subtracted from the receiving signal. Description of the same content as that of the first embodiment is omitted.

In other words, in the embodiment, as shown in FIG. 3, an ultrasonic diagnostic apparatus 34 includes the ultrasonic probe 2 and a control device 35, and the ultrasonic probe 2 and the control device 35 are connected to each other via the cable 4. The control device 35 has the control substrate 10, the input unit 11, the display unit 12, the power source unit 25, and a preprocessing substrate 36 as the circuit substrate, and the preprocessing substrate 36 is configured to have a first preprocessing substrate 37 and a second preprocessing substrate 38. Since the first preprocessing substrate 37 and the second preprocessing substrate 38 have the same circuit configuration, the first preprocessing substrate 37 is described, and the description of the second preprocessing substrate 38 is omitted.

The single second detecting amplifier 21 is installed in the first preprocessing substrate 37. Additionally, second ultrasonic wave amplifiers 39 are installed in the first preprocessing substrate 37, and the number of second ultrasonic wave amplifiers 39 is the same as the number of first ultrasonic wave amplifiers 17 installed in the first relay substrate 7. Additionally, the A/D converters 23 are installed in the first preprocessing substrate 37, and the number of A/D converters is the total number of the number of first detecting amplifiers 16 and the number of first ultrasonic wave amplifiers 17 installed in the first relay substrate 7.

Additionally, subtractors 40 are installed in the first preprocessing substrate 37, and the number of subtractors 40 is the same as the number of second ultrasonic wave amplifiers 39. The subtractor 40 is a circuit that subtracts one input data from the other input data. In the embodiment, for example, the subtractor 40 is configured of a programmable digital circuit. Hence, when a coefficient is multiplied to data corresponding to the noise signal, it is possible to easily change the coefficient. Additionally, the single P/S converting circuit 24 is installed in the first preprocessing substrate 37.

The input portion of the second detecting amplifier 21 is connected to the output portion of the first detecting amplifier 16 via the shielded wire 18. The output portion of the second detecting amplifier 21 is connected to one input portion of the A/D converter 23, and an output portion of the A/D converter 23 is connected to all of the input portions of the subtractors 40.

An Input portion of the second ultrasonic wave amplifier 39 is connected to the output portion of the single first ultrasonic wave amplifier 17 via the shielded wire 18. The output portion of the second ultrasonic wave amplifier 39 is connected to the single input portion the A/D converter 23, and the output portion of the A/D converter 23 is connected to the input portion of the single subtractor 40. The output portions of the subtractors 40 are connected to the P/S converting circuit 24.

The noise signal output from the first detecting amplifier 16 is amplified by the second detecting amplifier 21 and becomes the amplified noise signal. The amplified noise signal is input to the A/D converter 23, and the A/D converter 23 converts the amplified noise signal into the digital data. The amplified noise signal converted into the digital data is input to all of the subtractors 40.

The receiving signal output from the first ultrasonic wave amplifier 17 is amplified by the second ultrasonic wave amplifier 39. The receiving signal is input to the A/D converter 23, and the A/D converter 23 converts the receiving signal into the digital data. The receiving signal converted into the digital data is input to the single subtractor 40. The receiving element 15, the first ultrasonic wave amplifier 17, the second ultrasonic wave amplifier 39, the A/D converter 23, and the subtractor 40 are connected in series. The output portions of all of the subtractors 40 are connected to an input portion of the single P/S converting circuit 24. An output portion of the P/S converting circuit 24 is connected to the signal processing unit 27.

Next, a flow of a signal and data in the ultrasonic diagnostic apparatus 34 will be described. The first ultrasonic wave amplifier 17 amplifies the receiving signal and outputs the receiving signal to the second ultrasonic wave amplifier 39 via the shielded wire 18. The second detecting amplifier 21 amplifies the noise signal and outputs the amplified noise signal to the A/D converter 23. The A/D converter 23 converts the amplified noise signal into the digital data and outputs the digital data to all of the subtractors 40.

On the other hand, the second ultrasonic wave amplifier 39 receives and amplifies the receiving signal and outputs the amplified signal to the A/D converter 23. The A/D converter 23 converts the receiving signal into the digital data and outputs the digital data to the single subtractor 40. The integrated control unit 30 and the storage unit 31 are installed in the control device 35, and the data of coefficients that is used in the calculation by the subtractor 40 is stored in the storage unit 31. The integrated control unit 30 transmits the data of coefficients to the subtractors 40. The data of coefficients may be different for each of the subtractors 40 or may be the same value.

The subtractor 40 receives the amplified noise signal, the receiving signal, and the digital data of coefficients. Thus, the subtractor 40 subtracts a calculation result obtained by multiplying the amplified noise signal by the coefficient from the receiving signal. Hence, it is possible to subtract the calculation result obtained by multiplying by each individual coefficient for each of the subtractors 40 from the receiving signal. As a result, it is possible to easily adjust an amount that is subtracted from the receiving signal.

The subtractors 40 outputs the calculation result to the P/S converting circuit 24. The P/S converting circuit 24 converts parallel digital data of the calculation result into serial digital data and outputs the serial digital data to the signal processing unit 27. The content of the subsequent signal processing is the same as that of the first embodiment, and thus the description thereof is omitted.

Next, coefficients, which are used in the calculation by the subtractor 40, and calculation results will be described. In FIG. 4, the vertical axis represents values of coefficients, and an upper side has a larger value than a lower side in the figure. The horizontal axis represents numbers assigned to the subtractors 40. The receiving elements 15 are arranged in one direction in the ultrasonic element array 5. The number of receiving elements 15 arranged in one row is not particularly limited; however, in the embodiment, the number is reduced to 20 elements for easy understanding of the description.

The subtractors 40 are numbered from 1 to 20, and the numbers of the subtractors 40 are set to match the order of arrangement of the corresponding receiving elements 15. The subtractor 40 assigned a subtractor number of 10 is the subtractor 40 corresponding to the receiving element 15 that is positioned at the center. Subtractors 40 assigned subtractor numbers of 1 and 20 are subtractors 40 corresponding to the receiving elements 15 that are positioned at the ends. The coefficient line 41 represents coefficients that are set by the subtractors 40. As shown by the coefficient line 41, the coefficient corresponding to the receiving signal output from the receiving element 15 that is positioned at the center is set to be larger than the coefficient corresponding to the receiving signal output from the receiving element 15 that is positioned at the end.

In FIG. 5, the vertical axis represents values of noise outputs that are output by the A/D converter 23, and an upper side has a larger value than a lower side in the figure. The horizontal axis represents numbers assigned to the A/D converters 23. The A/D converter 23 having an A/D converter number of "0" is the A/D converter 23 connected to the second detecting amplifier 21. Hence, a noise output with the A/D converter number of "0" represents the amplified noise signal.

The A/D converter number is associated with the subtractor. In other words, for the A/D converter 23 and the subtractor 40, which are connected to each other via wiring, the A/D converter number and the subtractor number are the same number. Thus, the noise output line 42 represents the ultrasonic signal that is output by the A/D converter 23 when the transmitting element is not driven. As shown by the noise output line 42, the noise output that is output from the receiving element 15 that is positioned at the center is set to be larger than the noise output that is output from the receiving element 15 that is positioned at the end. A distribution of the noise output line 42 with the noise outputs is understood to be found because of an influence of the arrangement of the receiving elements 15 in the ultrasonic element array 5.

In FIG. 6, the vertical axis represents values of noise outputs that are output by the subtractor 40, and an upper side has a larger value than a lower side in the figure. The horizontal axis represents numbers assigned to the subtractors 40. Thus, the noise output line 43 represents the ultrasonic signal that is output by the subtractor 40 when the transmitting element is not driven. As shown by the noise output line 43, a noise output that is output from the subtractor 40 is substantially "0". This is because the coefficient line 41 is set as a time average value in the noise output line 42. Hence, the noise obtained by multiplying the amplified noise signal by the coefficient shown on the coefficient line 41 is subtracted from the noise output shown on the noise output line 42, and thereby the noise that is output from the subtractor 40 is suppressed.

When the same noise is added to the ultrasonic probe 2 and all of the circuit elements of the first preprocessing substrate 37, the first detecting amplifier 16 outputs the noise. Since the subtractor 40 subtracts the noise signal from the ultrasonic signal, it is possible to suppress the influence by the noise.

As described above, according to the embodiment, the following effects are achieved.

(1) According to the embodiment, the storage unit 31 stores a predetermined coefficient. Thus, the subtractor 40 subtracts the calculation result obtained by multiplying the amplified noise signal by the coefficient from the receiving signal. Hence, it is possible to subtract the calculation result obtained by multiplying by each individual coefficient for each of the subtractors 40 from the receiving signal. As a result, it is possible to easily adjust an amount that is subtracted from the receiving signal.

(2) According to the embodiment, the receiving elements 15 are arranged in one direction. Therefore, the receiving elements 15 include a receiving element that is positioned in a portion at an end of the arrangement and a receiving element that is positioned in a portion at the center of the arrangement. A noise signal that is included in the receiving signal which is output by the receiving element 15 positioned in the portion at the center of the arrangement is referred to as the noise signal of the central portion. A noise signal that is included in the receiving signal which is output by the receiving element positioned in the portion at the end of the arrangement is referred to as a noise signal of the end portion. At this time, the noise signal of the central portion is larger than the noise signal of the end portion.

A receiving signal which is output by the receiving element 15 positioned in the portion at the center of the arrangement is referred to as a receiving signal of the central portion. A receiving signal which is output by the receiving element 15 positioned in the portion at the end of the arrangement is referred to as a receiving signal of the end portion. Thus, the coefficient corresponding to the receiving signal of the central portion is larger than the coefficient corresponding to the receiving signal of the end portion. Hence, the noise signal of the central portion is more reduced than the noise signal of the end portion. As a result, it is possible to obtain the ultrasonic signal from which noise is reduced without an influence of the position of the arrangement of the receiving elements 15.

Third Embodiment

Figure 7:
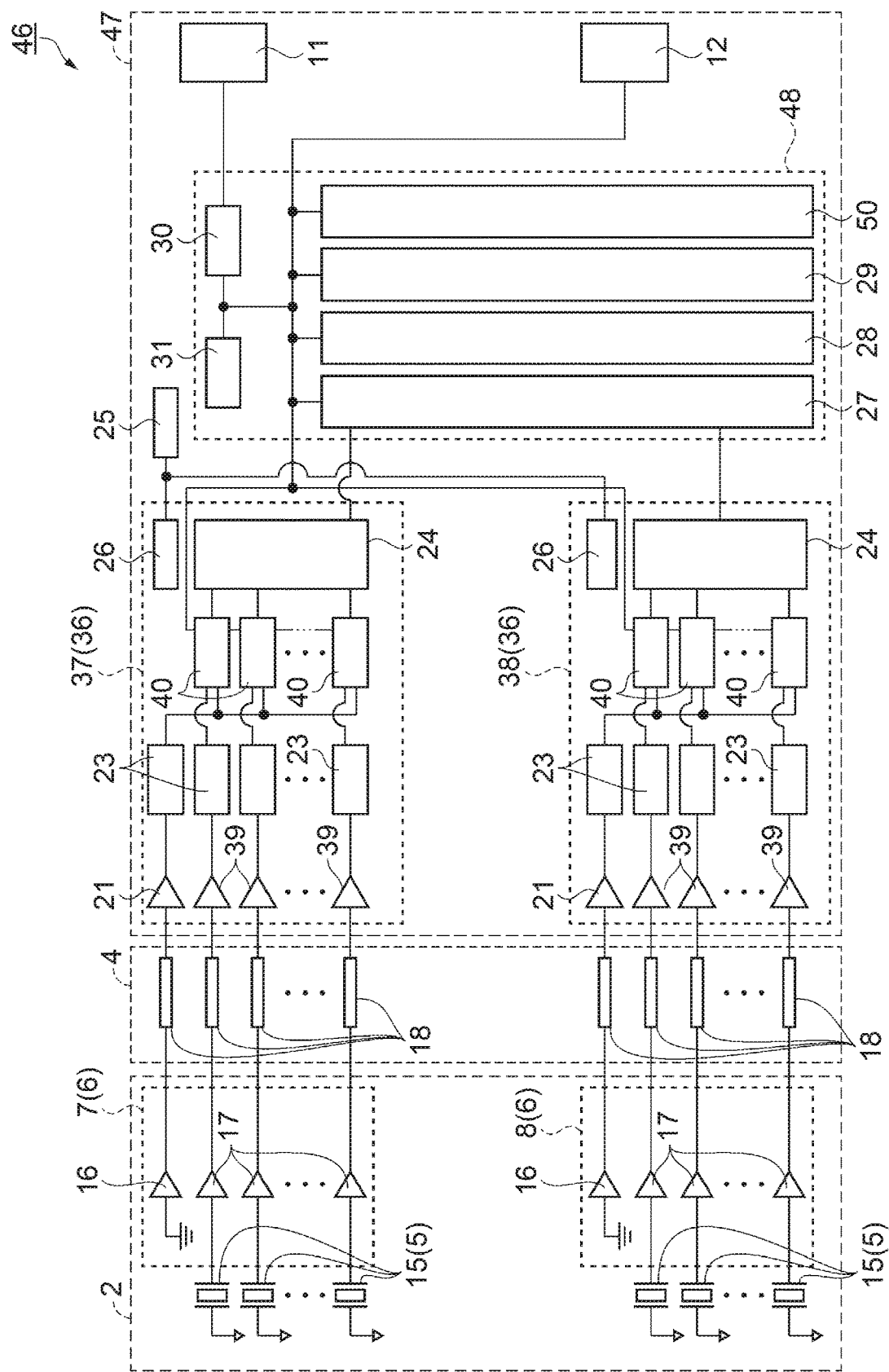
FIG. 7 is an electric circuit diagram of an ultrasonic diagnostic apparatus according to a third embodiment.

Next, an embodiment of the ultrasonic imaging apparatus will be described with reference to FIG. 7. FIG. 7 is an electric circuit diagram of the ultrasonic diagnostic apparatus. The embodiment differs from the second embodiment in that the ultrasonic diagnostic apparatus includes a coefficient calculating unit that computes the coefficient that is used in the calculation by the subtractor 40. Description of the same content as that of the second embodiment is omitted.

In other words, in the embodiment, as shown in FIG. 7, an ultrasonic diagnostic apparatus 46 includes a control device 47. The control device 47 includes a control substrate 48, in addition to the input unit 11, the display unit 12, the power source unit 25, and the preprocessing substrate 36. The control substrate 48 includes a coefficient calculating unit 50, in addition to the signal processing unit 27, the image processing unit 28, the display control unit 29, the integrated control unit 30, and the storage unit 31.

In a state in which the transmitting element is not driven, the receiving signal that is output by the receiving element 15 is used as a noise signal for reference. The coefficient calculating unit 50 calculates the coefficient from the distribution of noise signals for reference, which are output from the receiving elements 15 when an ultrasonic reflection signal is not detected. The calculation of the coefficient is performed in a state in which the transmitting element is not driven.

The first detecting amplifier 16 outputs the noise signal. The second detecting amplifier 21 amplifies the noise signal, and the A/D converter 23 converts the amplified noise signal into digital data. The subtractor 40 receives the digital data of the amplified noise signal and outputs the digital data of the amplified noise signal to the P/S converting circuit 24 without subtraction. The P/S converting circuit 24 converts the digital data of the amplified noise signal into serial data and outputs the serial data to the signal processing unit 27. The signal processing unit 27 converts the serial data back into the digital data of the amplified noise signal and stores the digital data to the storage unit 31.

The noise signal for reference that is output by the receiving element 15 is amplified by the first ultrasonic wave amplifier 17 and the second ultrasonic wave amplifier 39. The A/D converter 23 converts the noise signal for reference into the digital data. The subtractor 40 receives the digital data of the noise signal for reference and outputs the digital data of the noise signal for reference to the P/S converting circuit without subtraction. The P/S converting circuit 24 converts the digital data of the noise signal for reference into the serial data and outputs the serial data to the signal processing unit 27. The signal processing unit 27 converts the serial data back into the digital data of the noise signal for reference and stores the digital data to the storage unit 31. The signal processing unit 27 receives the digital data of the noise signal for reference for each receiving element 15 and stores the digital data to the storage unit 31.

The coefficient calculating unit 50 divides the digital data of the noise signal for reference for each of the receiving elements 15 by the digital data of the amplified noise signal. The divided result is used as the coefficient. The coefficient is calculated for each of the receiving elements 15. As a result, it is possible to obtain data corresponding to the coefficient line 41. The coefficients correspond to the distribution of the noise signals for reference.

As described above, according to the embodiment, the following effect is achieved.

(1) According to the embodiment, the ultrasonic diagnostic apparatus 46 includes the coefficient calculating unit 50. The coefficient calculating unit 50 calculates the coefficient from the distribution of the noise signals for reference, which are output from the receiving elements 15 when the ultrasonic reflection signal is not detected. Hence, it is possible to calculate the coefficient corresponding to the unique distribution of the noise signals for reference for each arrangement of the receiving elements 15. As a result, it is possible to subtract the noise signal from the receiving signal with higher accuracy.

Fourth Embodiment

Figure 8:
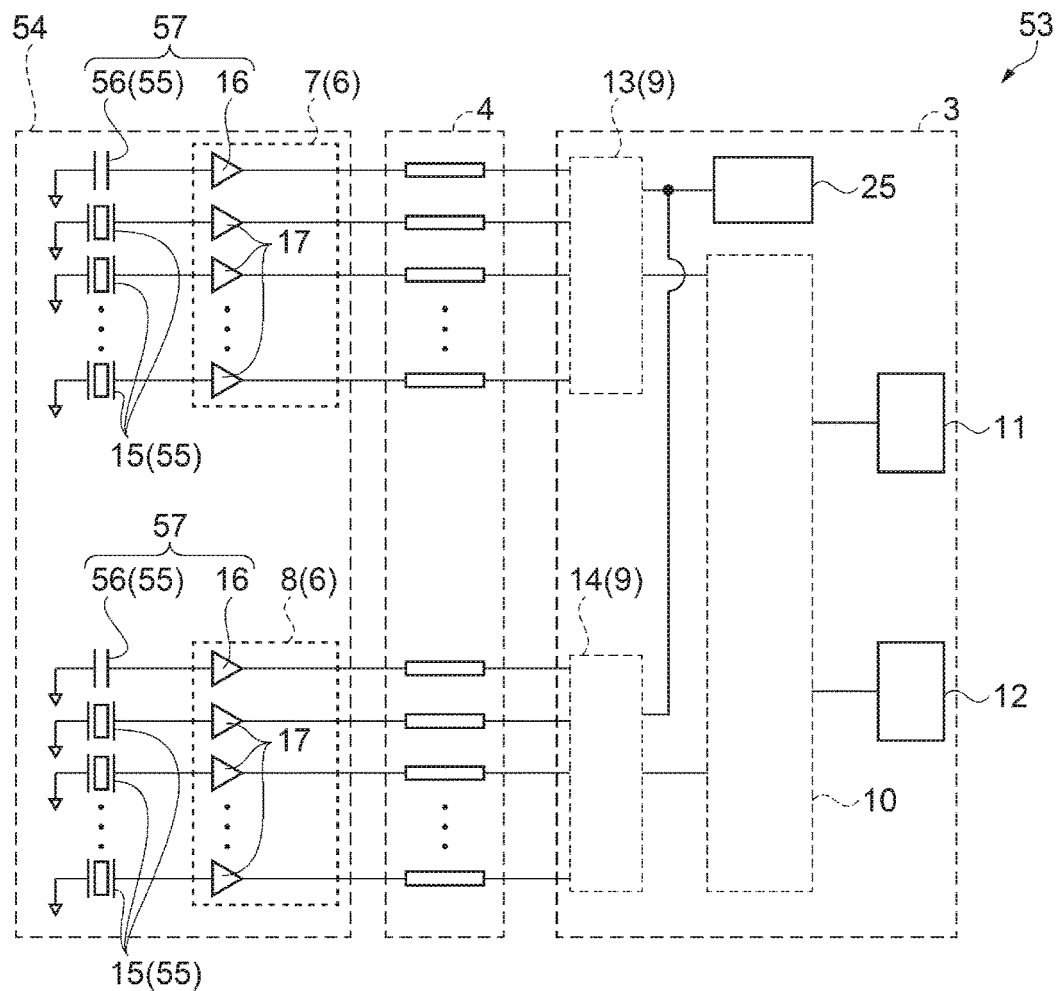
FIG. 8 is an electric circuit diagram of an ultrasonic diagnostic apparatus according to a fourth embodiment.
Figure 9:
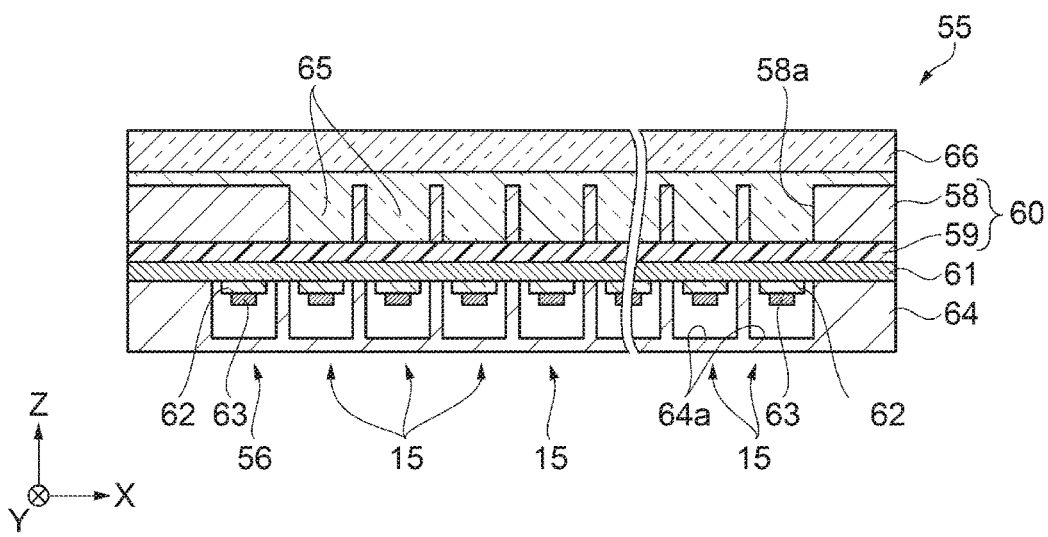
FIG. 9 is a schematic view for illustrating a structure of an ultrasonic element array.

Next, an embodiment of the ultrasonic imaging apparatus will be described with reference to FIGS. 8 and 9. FIG. 8 is an electric circuit diagram of the ultrasonic diagnostic apparatus, and FIG. 9 is a schematic view for illustrating a structure of the ultrasonic element array. The embodiment differs from the first embodiment in that the input portion of the first detecting amplifier 16 is provided with the same element as the ultrasonic element. Description of the same content as that of the first embodiment is omitted.

In other words, in the embodiment, as shown in FIG. 8, an ultrasonic diagnostic apparatus 53 includes the control device 3 and an ultrasonic probe 54. The control device 3 and the ultrasonic probe 54 are connected to each other via the cable 4. The ultrasonic probe 54 includes the relay substrate 6 and an ultrasonic element array 55, a noise detecting element 56, in addition to the receiving elements 15 are installed in the ultrasonic element array 55. The noise detecting element detects the noise signal. The relay substrate 6 is configured to have the first relay substrate 7 and the second relay substrate 8, and the first detecting amplifier 16 is installed in the first relay substrate 7 and the second relay substrate 8. The input portion of the first detecting amplifier 16 and the noise detecting element 56 are connected via wiring, and a noise detecting unit 57 is configured to have the first detecting amplifier 16 and the noise detecting element 56.

In FIG. 9, the ultrasonic element array 55 includes an element substrate 58 as the substrate, the element substrate 58 is provided with openings 58a, the number of openings are the same as the number of the receiving elements 15. The element substrate 58 has a rectangular plate shape, and a thickness direction is set as a Z direction. A longitudinal direction of the element substrate 58 is set as an X direction, and a direction orthogonal to the Z direction and the X direction is set as a Y direction. A vibration membrane 59 is installed on a side in a −Z direction of the element substrate 58 so as to be overlapped with the element substrate 58. The element substrate 58 and the vibration membrane 59 configure a substrate 60. The vibration membrane 59 is exposed through the opening 58a. The opening 58a is blocked by the vibration membrane 59, has a recessed shape, and corresponds to a recessed portion.

An upper electrode 61 is installed on the side in the −Z direction of the vibration membrane 59 so as to be overlapped with the vibration membrane 59. Piezoelectric membranes 62 are arranged and installed on the side in the −Z direction of the upper electrode 61 so as to be overlapped with the upper electrode 61. A lower electrode 63 is installed on the side in the −Z direction of the piezoelectric membrane 62 so as to be overlapped with the piezoelectric membrane 62. The receiving element 15 is configured to have the upper electrode 61, the piezoelectric membrane 62, and the lower electrode 63 at a position opposite to each of the openings 58a.

The upper electrode 61, the piezoelectric membrane 62, and the lower electrode 63 are installed even at a position which is not opposite to the opening 58a, and the upper electrode 61, the piezoelectric membrane 62, and the lower electrode 63 installed at the position which is not opposite to the opening 58a configure the noise detecting element 56. Hence, the noise detecting element 56 and the receiving element 15 are installed in the element substrate 58, the element substrate 58 at a position opposite to the receiving element 15 is thin, and the element substrate 58 at a position opposite to the noise detecting element 56 is thick. The noise detecting element 56 and the receiving element 15 have the same structure.

A sealing plate 64 is installed on the side in the −Z direction of the upper electrode 61 and the receiving element 15 so as to be overlapped with the upper electrode 61. The sealing plate 64 is provided with a recessed portion 64a corresponding to the receiving element 15 and the noise detecting element 56. The receiving element 15 and the noise detecting element 56 are stored inside the recessed portion 64a. The sealing plate 64 prevents the piezoelectric membrane from being degraded by attachment of moisture to the piezoelectric membrane 62.

An acoustic matching layer 65 is installed on a side in a +Z direction of the element substrate 58 and the opening 58a so as to be overlapped with the element substrate 58 and the opening 58a. An acoustic lens 66 is installed on the side in the +Z direction of the acoustic matching layer 65 so as to be overlapped with the acoustic matching layer 65.

A material of a region that configures the ultrasonic element array 55 is not particularly limited, and a material, which has a property required for the region, may be used. In the embodiment, for example, a silicon substrate is used as the element substrate 58 and the sealing plate 64. A membrane obtained by laminating silicon oxide and zirconium oxide is used for the vibration membrane 59. A membrane obtained by laminating an iridium oxide membrane and a platinum membrane for the upper electrode 61 and the lower electrode 63. Lead zirconatetitanate (PZT) is used for the piezoelectric membrane 62. A silicone resin is used for the acoustic matching layer 65 and the acoustic lens 66.

As described above, according to the embodiment, the following effects are achieved.

(1) According to the embodiment, the noise detecting unit 57 includes the noise detecting element 56 that outputs the noise signal. The noise detecting element 56 and the receiving element 15 have the same structure. Hence, the noise detecting element 56 is capable of detecting a noise signal having the same intensity as the noise signal that is included in the receiving signal which is output by the receiving element 15.

(2) According to the embodiment, the noise detecting element 56 and the receiving element 15 are installed in the element substrate 58. The element substrate 58 is provided with the opening 58a. The receiving element 15 is installed at a position opposite to the opening 58a, and the noise detecting element 56 is installed at a position that is not opposite to the opening 58a. The thickness of the substrate 60 at the position opposite to the receiving element 15 is the thickness of the vibration membrane 59 and is not small, and thus the substrate vibrates due to the ultrasonic wave at the position. On the other hand, the thickness of the substrate 60 at the position opposite to the noise detecting element 56 is not large but is a thickness obtained by adding the thicknesses of the element substrate 58 and the vibration membrane 59, and thus the substrate is unlikely to vibrate due to the ultrasonic wave at the position. Hence, the receiving element 15 receives the ultrasonic wave, the noise detecting element 56 is unlikely to be influenced by the ultrasonic wave, and thus it is possible to easily detect the noise.

(3) According to the embodiment, a structure in which the opening 58a is formed at the position opposite to the receiving element 15, and the opening 58a is not formed at the position that is not opposite to the noise detecting element 56 is employed. Since the opening 58a is formed through patterning of the element substrate 58, it is possible to easily form a pattern of the opening 58a.

Fifth Embodiment

Figure 10:
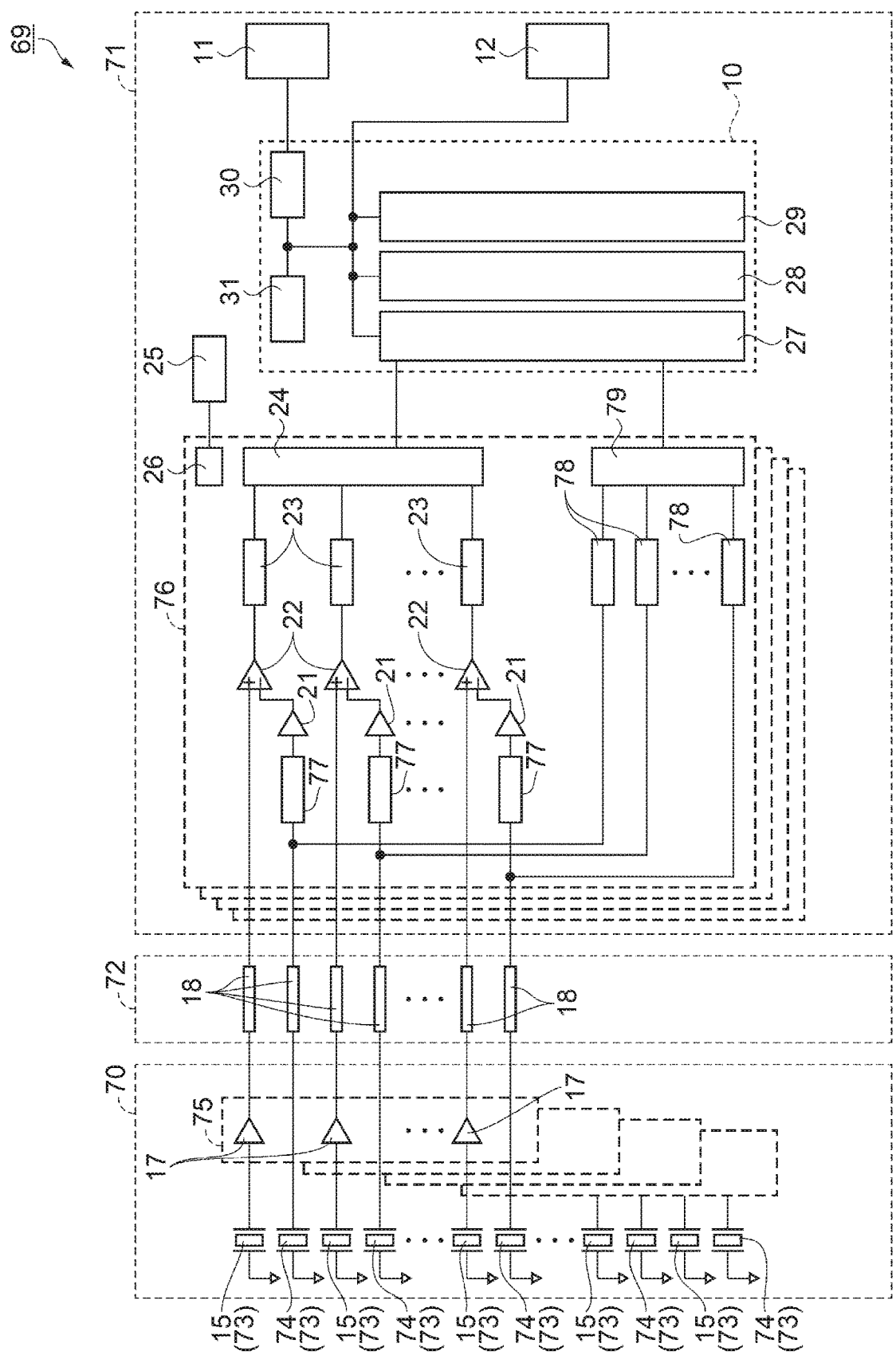
FIG. 10 is an electric circuit diagram of an ultrasonic diagnostic apparatus according to a fifth embodiment.

Next, an embodiment of the ultrasonic imaging apparatus will be described with reference to FIG. 10. FIG. 10 is an electric circuit diagram of the ultrasonic diagnostic apparatus. The embodiment differs from the first embodiment in that the transmitting element serves as the noise detecting element. Description of the same content as that of the first embodiment is omitted.

In other words, in the embodiment, as shown in FIG. 10, an ultrasonic diagnostic apparatus 69 includes an ultrasonic probe 70 and a control device 71, and the ultrasonic probe 70 and the control device 71 are connected to each other via the cable 72. An ultrasonic element array 73 is installed in the ultrasonic probe 70, and the plurality of the receiving elements 15 and the plurality of transmitting element 74 are installed in an ultrasonic element array 73 in a matrix shape. The receiving element 15 receives the ultrasonic wave, converts the ultrasonic wave into the electric signal, and outputs a receiving signal. The transmitting element 74 transmits the ultrasonic wave intermittently. The transmitting element 74 has a structure in which the ultrasonic wave is easily emitted and has a structure in which receiving sensitivity is low. Hence, when a reflected wave of the ultrasonic wave reaches the ultrasonic element array 73, the receiving element 15 outputs the receiving signal, and the transmitting element 74 is difficult to output the receiving signal.

Additionally, the plurality of relay substrates 75 are installed in the ultrasonic probe 70. The plurality of first ultrasonic wave amplifiers 17 are installed in the relay substrate 75, and some receiving elements 15 are connected to the input portion of the first ultrasonic wave amplifier 17. The plurality of shielded wires 18 are installed in the cable 72.

The control device 71 has the preprocessing substrate 76 as the plurality of circuit substrate, in addition to the control substrate 10, the input unit 11, the display unit 12, and the power source unit 25. The number of preprocessing substrates 76 and the number of relay substrate 75 are the same as each other, and the single preprocessing substrate 76 and the single relay substrate 75 are connected to each other via cable 72.

The plurality of subtraction amplifiers 22 are installed in the preprocessing substrate 76. The number of subtraction amplifiers 22 installed in the preprocessing substrate 76 is the same as the number of first ultrasonic wave amplifiers 17 installed in the relay substrate 75. The output portions of the first ultrasonic wave amplifiers 17 of the relay substrate 75 are connected to the +input portions of the subtraction amplifiers 22 of the preprocessing substrate 76 via the shielded wires 18.

A plurality of switches 77 and the plurality of second detecting amplifiers 21 are installed in the preprocessing substrate 76. The single transmitting element 74 is connected to the input portion of the switch 77 via the shielded wire 18. Further, the output portion of the switch 77 is connected to the input portion of the second detecting amplifier 21 via wiring. The output portion of the second detecting amplifier 21 is connected to the input portion of the subtraction amplifier 22.

One receiving element 15, one transmitting element 74, and one subtraction amplifier 22 configure one set. The receiving element 15 and the transmitting element 74 which are connected to the same subtraction amplifier 22 belong to the same set. The receiving element 15 and the transmitting element 74 of the same set are disposed to be adjacent to each other. When the transmitting element 74 does not emit the ultrasonic wave, the switch 77 is short-circuited. The transmitting element 74 detects the noise and functions as the noise detecting element that outputs the noise to the second detecting amplifier 21. The transmitting element 74 outputs the noise signal to the second detecting amplifier 21. The second detecting amplifier 21 outputs the amplified noise signal to the subtraction amplifier 22.

In this manner, the receiving signal is input to the +input portion of the subtraction amplifier 22, and the amplified noise signal is input to the −input portion thereof. Thus, the subtraction amplifier 22 corresponds to a subtracting unit that subtracts the amplified noise signal from the receiving signal. The subtraction amplifier 22 computes the ultrasonic signal. The A/D converters 23 are installed in the preprocessing substrate 76, and the number of A/D converters is the same as the number of subtraction amplifiers 22. The A/D converter receives the ultrasonic signal that is output by the subtraction amplifier 22 and converts the ultrasonic signal into the digital signal.

The P/S converting circuit 24 is installed in the preprocessing substrate 76. An output from each of the A/D converter 23 is parallel data, and the P/S converting circuit 24 converts the parallel data into serial data and transmits the serial data to the control substrate 10.

Transmitting circuits 78 and a single transmission wave forming circuit 79 are installed in the preprocessing substrate 76, and the number of transmitting circuits 78 is the same as the number of subtraction amplifiers 22. The transmission wave forming circuit 79 is a circuit that forms a waveform for driving the transmitting element 74 by matching the timing of the ultrasonic wave that is output by the transmitting elements 74. The transmitting circuit 78 is a circuit that amplifies the driving waveform with electric power suitable for the driving of the transmitting element 74. The transmitting circuit 78 is connected to the transmitting element 74 via the shielded wire 18, and the transmitting circuit 78 is connected to the transmission wave forming circuit 79. The transmission wave forming circuit 79 is connected to the signal processing unit 27.

Next, an operation of the ultrasonic diagnostic apparatus 69 will be described. The transmission wave forming circuit 79 receives an instruction signal from the signal processing unit 27, forms a drive waveform, and outputs the drive waveform to the transmitting circuit 78. The transmitting circuit 78 amplifies the drive waveform with electric power and outputs the drive waveform to the transmitting element 74. At this time, the switch 77 is not to be opened and the signal is not to flow. The transmitting element 74 drives the vibration membrane 59 based on the drive waveform, and emits the ultrasonic wave. The switch 77 is closed after the ultrasonic wave is emitted.

The ultrasonic wave travels into the internal part of the subject 19, a part of reflected wave reaches the receiving element 15. The receiving element 15 outputs the receiving signal to the first ultrasonic wave amplifier 17. The first ultrasonic wave amplifier 17 outputs the amplified receiving signal to the +input portion of the subtraction amplifier 22.

The transmitting element 74 outputs the noise signal to the second detecting amplifier 21 without responding to the reflected wave of the ultrasonic wave. The noise signal is the electromagnetic noise or the power-supply noise and the noise that is received by the receiving element 15 and the transmitting element 74. The transmitting element 74 serves as the noise detecting element that detects the noise and outputs the noise signal when the transmitting element does not transmit the ultrasonic wave. Hence, the plurality of noise detecting elements.

The second detecting amplifier 21 outputs the amplified noise signal, which is obtained by amplifying the noise signal) to the −input portion of the subtraction amplifier 22. The subtraction amplifier 22 subtracts the amplified noise signal from the receiving signal. The subtraction amplifier 22 outputs the computed ultrasonic signal to the A/D converter 23. An operation of the A/D converter 23 is the same as that of the first embodiment, and the description thereof is omitted.

As described above, according to the embodiment, the following effects are achieved.

(1) According to the embodiment, one receiving element 15, one transmitting element 74, and one subtraction amplifier configure one set. The receiving element 15 and the transmitting element 74 in the same set are disposed to be adjacent to each other. Equivalent electromagnetic noise is applied to both of the adjacent receiving element 15 and noise detecting element 74. The subtraction amplifier 22 can remove, from the receiving signal, the noise signal equivalent to the noise signal that is added to the receiving signal. Hence, it is possible to remove the noise signal from the receiving signal with high accuracy.

(2) According to the embodiment, the ultrasonic diagnostic apparatus 69 includes the transmitting element 74 that transmits the ultrasonic wave intermittently. The transmitting element 74 serves as the noise detecting element, and the transmitting element 74 outputs the noise signal when the transmitting element does not transmit the ultrasonic wave. Hence, the noise detecting element may be provided separately from the transmitting element 74, and thus it is possible to manufacture the ultrasonic diagnostic apparatus 69 with high productivity.

The embodiment is not limited to the embodiments described above, and it is possible for those who have common knowledge in the art to perform various modifications and improvements within the technical ideas of the present invention. Hereinafter, modification examples will be described.

MODIFICATION EXAMPLE 1

In the first embodiment, the input portion of the first detecting amplifier 16 is grounded. The noise detecting element 56 or the transmitting element 74 may be connected to the input portion of the first detecting amplifier 16. At this time, it is also possible to output the electromagnetic noise to the first detecting amplifier 16.

MODIFICATION EXAMPLE 2

In the fifth embodiment, the subtraction amplifier 22 subtracts the amplified noise signal from the receiving signal. As described in the second embodiment, after performing conversion into the digital data by the A/D converter 23, the subtractor 40 may subtract the amplified noise signal from the receiving signal. Further, as described in the third embodiment, the coefficient calculating unit 50 may calculate the coefficient.

MODIFICATION EXAMPLE 3

In the fifth embodiment, the transmitting element 74 and the transmitting circuit 78 are always connected to each other. Hence, a bypass voltage is applied to the transmitting element 74. A configuration, in which a switching element is installed between the transmitting element 74 and the transmitting circuit 78, and the bypass voltage is not applied to the transmitting element 74 during receiving, may be employed. It is possible to reduce the influence by the bypass voltage.

The invention claimed is:

1. An ultrasonic diagnostic apparatus comprising:
a plurality of circuit substrates including a first circuit substrate and a second circuit substrate that are stacked on each other;
a plurality of receiving elements disposed on an ultrasonic probe connected to the plurality of circuit substrates and arranged in a matrix on the ultrasonic probe, each of the plurality of receiving elements being configured to receive an ultrasonic wave, convert the ultrasonic wave into an electric signal, and output a receiving signal, the plurality of receiving elements including a first receiving element and a second receiving element, the first receiving element being configured with a first group of receiving elements, the second receiving element being configured with a second group of receiving elements;
a plurality of relay substrates disposed in the ultrasonic probe, the plurality of relay substrates including a first relay substrate and a second relay substrate that are stacked on each other;
a plurality of noise detectors, each of the plurality of noise detectors being configured to detect noise and output a noise signal, the plurality of noise detectors including a first noise detector and a second noise detector disposed on the first relay substrate and the second relay substrate, respectively, the first noise detector detecting noise of the receiving signal from the first group of receiving elements, the second noise detector detecting noise of the receiving signal from the second group of receiving elements;
a plurality of noise signal amplifiers, each of the plurality of noise signal amplifiers being configured to amplify the noise signal and output an amplified noise signal, the plurality of noise signal amplifiers including a first noise signal amplifier and a second noise signal amplifier, the first and second noise signal amplifiers receiving the noise signals from the first and second noise detectors, respectively;
a plurality of subtracting elements, each of the plurality of subtracting elements being configured to receive the receiving signal and the amplified noise signal and subtract the amplified noise signal from the receiving signal, the plurality of subtracting elements including a first subtracting element and a second subtracting element, the first and second subtracting elements receiving the receiving signals from the first and second receiving elements and the amplified noise signals from the first and second noise signal amplifiers, and subtracting the amplified noise signals from the receiving signals, respectively; and a memory configured to store coefficients including a first coefficient and a second coefficient, wherein the first circuit substrate has the first noise signal amplifier and the first subtracting element, and the second circuit substrate has the second noise signal amplifier and the second subtracting element, each of the plurality of subtracting elements subtracts a calculation result obtained by multiplying the amplified noise signal by a corresponding one of the coefficients, the first coefficient corresponds to the receiving signal outputted from the first receiving element that is positioned at a center of the matrix of each of the first and second groups of receiving elements of the plurality of receiving elements, the second coefficient corresponds to the receiving signal outputted from the second receiving element that is positioned at an end of each of the first and second groups of receiving elements of the matrix of the plurality of receiving elements, the first coefficient is larger than the second coefficient, and the plurality of circuit substrates are disposed in a controller that is independently provided from the ultrasonic probe, and the first and second relay substrates and the first and second circuit substrates are electrically connected to each other, respectively.

2. The ultrasonic diagnostic apparatus according to claim 1, wherein each of the plurality of noise detectors includes a noise detecting element that outputs the noise signal, and wherein the noise detecting element and each of the plurality of receiving elements have the same structure.

3. The ultrasonic diagnostic apparatus according to claim 2, wherein the noise detecting element and one of the plurality of receiving elements are installed on a corresponding one of the plurality of relay substrates, and wherein a thickness of the corresponding one of the plurality of relay substrates at a position opposite to the one of the plurality of receiving elements is smaller than a thickness of the corresponding one of the plurality of relay substrates at a position opposite to the noise detecting element.

4. The ultrasonic diagnostic apparatus according to claim 1, wherein one of the plurality of circuit substrates is provided with a switching circuit installed to supply a power source.

5. An ultrasonic diagnostic apparatus comprising:

a plurality of circuit substrates including a first circuit substrate and a second circuit substrate that are stacked on each other;

a plurality of receiving elements disposed on an ultrasonic probe connected to the plurality of circuit substrates and arranged in a matrix on the ultrasonic probe, each of the plurality of receiving elements being configured to receive an ultrasonic wave, convert the ultrasonic wave into an electric signal, and output a receiving signal, the plurality of receiving elements including a first receiving element and a second receiving element, the first receiving element being configured with a first group of receiving elements, the second receiving element being configured with a second group of receiving elements;

a plurality of relay substrates disposed in the ultrasonic probe, the plurality of relay substrates including a first relay substrate and a second relay substrate that are stacked on each other;

a plurality of noise detectors, each of the plurality of noise detectors being configured to detect noise and output a noise signal, the plurality of noise detectors including a first noise detector and a second noise detector disposed on the first relay substrate and the second relay substrate, respectively, the first noise detector detecting noise of the receiving signal from the first group of receiving elements, the second noise detector detecting noise of the receiving signal from the second group of receiving elements;

a plurality of subtracting elements, each of the plurality of subtracting elements being configured to receive the receiving signal and the noise signal and subtract the noise signal from the receiving signal, the plurality of subtracting elements including a first subtracting element and a second subtracting element, the first and second subtracting elements receiving the receiving signals from the first and second receiving elements and the noise signals from the first and second noise detectors, and subtracting the noise signals from the receiving signals, respectively; and a memory configured to store coefficients including a first coefficient and a second coefficient, wherein the first circuit substrate has the first subtracting element, and the second circuit substrate has the second subtracting element, each of the plurality of subtracting elements subtracts a calculation result obtained by multiplying the noise signal by a corresponding one of the coefficients, the first coefficient corresponds to the receiving signal outputted from the first receiving element that is positioned at a center of the matrix of each of the first and second groups of receiving elements of the plurality of receiving elements, the second coefficient corresponds to the receiving signal outputted from the second receiving element that is positioned at an end of each of the first and second groups of receiving elements of the matrix of the plurality of receiving elements, and the first coefficient is larger than the second coefficient, the first receiving element and the first noise detector are located adjacent to each other in the first relay substrate, and the second receiving element and the second noise detector are located adjacent to each other in the second relay substrate, and the plurality of circuit substrates are disposed in a controller that is independently provided from the ultrasonic probe, and the first and second relay substrates and the first and second circuit substrates are electrically connected to each other, respectively.

6. The ultrasonic diagnostic apparatus according to claim 5, further comprising:

a transmitting element configured to transmit the ultrasonic wave, wherein the transmitting element serves as one of the plurality of noise detectors when the transmitting element does not transmit the ultrasonic wave.

* * * * *